United States Patent
Rosenberg

(10) Patent No.: US 6,314,322 B1
(45) Date of Patent: *Nov. 6, 2001

(54) SYSTEM AND METHOD FOR TREATING DILATED CARDIOMYOPATHY USING END DIASTOLIC VOLUME (EDV) SENSING

(75) Inventor: Meir Rosenberg, Newton, MA (US)

(73) Assignee: Abiomed, Inc., Danvers, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,697

(22) Filed: Mar. 2, 1998

(51) Int. Cl.[7] .................................................. A61N 1/36

(52) U.S. Cl. ................................. 607/17; 607/9; 607/24

(58) Field of Search .............................. 607/6, 9, 5, 24, 607/119, 17; 600/374, 390

(56) References Cited

U.S. PATENT DOCUMENTS

| | | | |
|---|---|---|---|
| 3,871,359 | 3/1975 | Pacela | 128/2.1 |
| 4,112,953 | 9/1978 | Shanker et al. | 128/419 |
| 4,303,075 | 12/1981 | Heilman et al. | 128/419 |
| 4,399,820 | 8/1983 | Wirtzfeld et al. | 128/419 |
| 4,436,092 | 3/1984 | Cook et al. | 128/419 |
| 4,476,874 | 10/1984 | Taenzer et al. | 128/663 |
| 4,535,774 | 8/1985 | Olson | 128/419 |
| 4,590,944 | 5/1986 | Mann et al. | 128/419 |
| 4,686,987 | 8/1987 | Salo et al. | 128/419 |
| 4,730,619 | 3/1988 | Koning et al. | 128/419 |
| 4,733,667 | 3/1988 | Olive et al. | 128/419 |
| 4,802,481 | 2/1989 | Schroeppel | 128/419 |

(List continued on next page.)

FOREIGN PATENT DOCUMENTS

| | | | |
|---|---|---|---|
| 0503839 | 9/1992 | (EP) | A61B/8/06 |
| 0591642 | 4/1994 | (EP) | A61N/1/365 |
| WO 9743001 WO | 11/1997 | (WO) | A61N/1/362 |
| 9806454A | 2/1998 | (WO) | A61N/1/365 |

OTHER PUBLICATIONS

Lau, Chu–Pak, The Range of Sensors and Algorithms Used in Rate Adaptive Cardiac Pacing, *Pace*, vol. vol. 15 (1992), pp. 11771211.

*Primary Examiner*—Carl Layno
(74) *Attorney, Agent, or Firm*—Thomas J. Engellenner; Ronald E. Cahill; Nutter, McClennen & Fish, LLP

(57) ABSTRACT

A system for controlling end diastolic volume of the heart is disclosed. The system includes an EDV sensor constructed and arranged to measure a parameter related to the end diastolic volume of the heart, and a heart stimulator, responsive to the EDV sensor, constructed and arranged to invoke systole when the measured parameter reaches a predetermined level, the parameter reaching that level prior to termination of diastole. Preferably, the heart stimulator may be a pacemaker. The EDV sensor may be any sensor constructed to measure a parameter related to the end diastolic volume of the heart, or another selected physiological or patho-physiological condition of the heart, including a strain sensor, a stress sensor, a dimension sensor, an impedance sensor, an optical sensor, a microwave sensor, or another sensor constructed to measure a parameter related to the end diastolic volume of the heart, or another selected physiological or patho-physiological condition of the heart. A method for controlling end diastolic volume of the heart including the steps of measuring a parameter that is related to the end diastolic volume of the heart, and invoking systole before termination of diastole when the measured parameter reaches a predetermined level is also disclosed.

30 Claims, 5 Drawing Sheets

U.S. PATENT DOCUMENTS

| | | | |
|---|---|---|---|
| 4,813,952 | 3/1989 | Khalafalla | 623/3 |
| 4,974,511 | 12/1990 | Hsi-Chou | 101/38.1 |
| 4,995,390 | 2/1991 | Cook et al. | 128/419 |
| 5,003,976 | 4/1991 | Alt | 128/419 |
| 5,007,927 | 4/1991 | Badylak et al. | 623/3 |
| 5,081,988 | 1/1992 | Cook et al. | 128/419 |
| 5,094,244 | 3/1992 | Callahan et al. | 128/677 |
| 5,137,019 | 8/1992 | Pederson et al. | 128/419 |
| 5,139,020 | 8/1992 | Koestner et al. | 128/419 |
| 5,154,171 * | 10/1992 | Chirife | 607/24 |
| 5,174,286 * | 12/1992 | Chirife | 607/11 |
| 5,184,615 | 2/1993 | Nappholz et al. | 128/419 |
| 5,235,975 | 8/1993 | Gang et al. | 607/108 |
| 5,259,395 | 11/1993 | Li | 607/131 |
| 5,318,595 | 6/1994 | Ferek-Petric et al. | 607/17 |
| 5,324,323 | 6/1994 | Bui | 607/119 |
| 5,383,873 | 1/1995 | Hoeu et al. | 607/891.1 |
| 5,417,715 | 5/1995 | Noren et al. | 607/9 |
| 5,417,717 * | 5/1995 | Salo et al. | 607/18 |
| 5,423,869 | 6/1995 | Poore et al. | 607/18 |
| 5,423,870 | 6/1995 | Olive et al. | 607/18 |
| 5,464,420 | 11/1995 | Hori et al. | 606/202 |
| 5,480,441 | 1/1996 | Hudrlik | 607/17 |
| 5,498,254 | 3/1996 | Hoey et al. | 604/891.1 |
| 5,507,785 | 4/1996 | Deno | 607/24 |
| 5,531,772 | 7/1996 | Prutchi | 607/17 |
| 5,542,915 | 8/1996 | Edwards et al. | 604/22 |
| 5,549,653 | 8/1996 | Stotts et al. | 607/4 |
| 5,562,595 | 10/1996 | Neisz | 600/16 |
| 5,824,019 | 10/1998 | Rueter et al. | 607/17 |

* cited by examiner

SYSTEM AND METHOD FOR TREATING DILATED CARDIOMYOPATHY USING END DIASTOLIC VOLUME (EDV) SENSING

BACKGROUND OF THE INVENTION

1. Field of the Invention

The present invention relates generally to controlling congestive heart failure and, more particularly, to electrically controlling a dilated condition resulting from congestive heart failure.

2. Related Art

The heart pumps blood through a patient's body in order to carry oxygen to, and remove carbon dioxide from, cells located throughout the body. In a patient having a normal heart, the rate at which the blood is pumped through the body increases or decreases to accommodate changes in the physiological needs of the patient. That is, as the cells of the patient's body require more oxygen, the heart rate and/or stroke volume increases to pump more oxygen-rich blood to the cells. When insufficient oxygen is available from the lungs, the respiration rate may also increase to increase the rate of oxygen intake into the body. Conversely, as the demand for oxygen decreases, the heart rate decreases, providing less blood flow and, hence, less oxygen, to the cells.

During a heart cycle, deoxygenated, venous blood enters the right atrium of the heart via the inferior vena cava and the superior vena cava and, during diastole, flows to the right ventricle. The pulmonary artery then delivers blood ejected from the right ventricle into the lungs. The pulmonary vein carries oxygenated blood from the lungs to the left atrium of the heart. During diastole, oxygenated blood flows from the left atrium to the left ventricle, which is filled to its end diastolic volume (EDV). During systole the left ventricle ejects oxygenated blood into the aorta.

The ventricles are cone-shaped muscular chambers that continuously change their shape during the heart cycle. The proper functioning of each ventricle is critically related to its internal dimension, wall thickness and the electrical states of the myocytes. In a normal heart, the left ventricle empties between 56% and 78% of its volume in systole; that is, the stroke volume is between 56% and 78% EDV.

Congestive heart failure (CHF) is a condition in which the heart is unable to provide the necessary amount of oxygenated blood to the body. CHF may be caused by any number of conditions, including high blood pressure, heart valve defects, congenital heart defects, myocardial infarction, irregular heart beat or pulmonary disease. Generally, CHF leads to a progressive dilatation of the heart. This dilatation is typically preceded by compensatory hypertrophy of the heart, or a thickening of the walls of the heart in response to vascular, valvular, or other heart disease. Progressive dilation of the heart increases the risk of developing dilated cardiomyopathy, which is a condition where the ventricles of the heart are weakened to the extent that they contract with less-than-optimal force during systole. This reduction in the systolic function can cause diminished stroke volume and reduced cardiac output.

The more dilated the heart becomes, the less it is able to contract and pump blood from the left ventricle into the aorta. The blood remaining in the heart increases the end-diastolic pressure in the left or right ventricle and, over time, increases the end diastolic volume. The elevated diastolic pressure is also transmitted through the pulmonary vein or artery to the lungs increasing pulmonary capillary pressure. An increase in pulmonary capillary pressure, in turn, can lead to the filling of the lungs with fluid, known as pulmonary edema. With pulmonary edema, breathing becomes more difficult, resulting in dyspnea, orthopnea and/or tachypnea. Furthermore, elevated right ventricular diastolic pressure increases the systemic venous pressure, which leads to peripheral venous congestion and edema.

Another symptom of dilated cardiac myopathy is inadequate blood flow to vital organs due to decreased cardiac output. Resulting problems may include decreased cerebral blood flow, impairing central nervous system function; and reduced blood profusion of the liver and kidneys, impairing hebetic and renal function. If left untreated, the heart's function progressively deteriorates, ultimately resulting in death.

Current treatment of dilated cardiomyopathy generally includes drug treatment. Common treatments include the use of diuretics, digitalis and angiotensin-converting enzyme inhibitors and anticoagulants. However, drug treatment typically does not return the heart to its normal physiological state.

What is needed, therefore, is a system and method that controls the dilatative effects of congestive heart failure, returning the heart to a more normal physiological state without compromising cardiac output or increasing the metabolic needs of the heart. That is, what is needed is a technique that prevents dilation of the heart which leads to the heart's reduced work capacity.

SUMMARY OF THE INVENTION

In one aspect of the present invention, a system for controlling end diastolic volume (EDV) of the heart is disclosed. The system includes an EDV sensor constructed and arranged to measure a parameter related to the end diastolic volume of the heart, and a heart stimulator, responsive to the EDV sensor, constructed and arranged to invoke systole when the measured parameter reaches a predetermined level, the parameter reaching that level prior to termination of diastole. Preferably, the heart stimulator may be a pacemaker. The EDV sensor may be any sensor constructed to measure a parameter related to the end diastolic volume of the heart, or another selected physiological or patho-physiological condition of the heart related to the onset of a compromise in this contractible function of the heart.

In one embodiment of this aspect of the invention, the EDV sensor is a stress/strain sensor. In this embodiment, the strain sensor includes an expandable element implanted on a wall of the heart. Preferably, the expandable element at least partially encircles the heart.

In another embodiment of this aspect of the invention, the EDV sensor is a dimensional sensor. This sensor includes a transmitter constructed and arranged to emit sound waves into the heart; and a receiver constructed and arranged to detect sound waves reflected from various surfaces of the heart. Preferably, the transmitter and receiver include at least one piezoelectric crystal. In one embodiment, the dimensional sensor further includes a coupling medium attached to the piezoelectric crystal, wherein the coupling medium is implantably attachable to a wall of the heart. In one embodiment, the receiver is constructed and arranged to detect multiple sound waves reflected from tissue interfaces in the heart. In a preferred embodiment, the dimensional sensor is further constructed to measure dimensional changes within the myocardium of the heart to afford a measure of stress in the heart wall in accordance with the following equation:

$$\sigma = \frac{Pr}{\tau}$$

where σ is the stress, P is ventricular pressure, r is the measured ventricular radius and τ is the measured ventricular wall thickness. The stress sensor is further constructed to calculate the ventricular thickness (τ) as a product of a time interval between a first reflected signal and a second reflected signal, and the speed of sound within the heart wall. The stress sensor is further constructed to calculate the ventricular radius (r) by employing the following equation:

$$r = \frac{T_E - T_D}{4} C_B$$

where $T_E$ is detected time of a third reflected signal, $T_D$ is detected time of a second reflected signal, and $C_B$ is speed of sound in blood.

In another embodiment of this aspect of the invention, the EDV sensor is solely a dimensional sensor. In one embodiment, the dimension sensor includes a band that at least partially encircles the heart to monitor a circumference of the heart. In another embodiment, the dimension sensor includes a band that at least partially encircles the heart, the band including a selected fixed circumference.

In still other embodiments, of this aspect of the invention, the EDV sensor is an impedance sensor, an optical sensor, a microwave sensor, or another sensor constructed to measure a parameter related to the end diastolic volume of the heart, or another selected physiological or patho-physiological condition of the heart.

In another aspect of the invention, a method for controlling end diastolic volume of the heart is disclosed. The method includes the steps of measuring a parameter that is related to the end diastolic volume of the heart, and invoking systole before termination of diastole when the measured parameter reaches a predetermined level.

In one embodiment, the measuring step includes measuring strain experienced by an expandable element implanted on a wall of the heart. In another embodiment, the measuring step includes the step of measuring stress in a wall of the heart. In this embodiment, the stress measuring step includes the steps of: emitting from a transmitter sound waves into the heart; and detecting by a receiver sound waves reflected from the heart. Preferably, the emitting and detecting steps include the step of introducing the sound waves into a coupling medium implantably attached to the heart wall. It is also preferable that the detecting step includes the step of detecting multiple sound waves reflected from tissue interfaces in the heart. In this embodiment, the stress measuring step includes the step of calculating myocardium stress by employing the following equation:

$$\sigma = \frac{Pr}{\tau}$$

where σ is the stress, P is ventricular pressure, r is ventricular radius and τ is ventricular wall thickness. The stress measuring step further includes the step of calculating the ventricular radius (r) by employing the following equation:

$$r = \frac{T_E - T_D}{4} C_B$$

where $T_E$ is detection time of a third reflected signal, $T_D$ is detected time of a second reflected signal, and $C_B$ is the speed of sound in blood.

In this embodiment, the measuring step further includes the step of: calculating the ventricular thickness (τ) as a product of an elapsed time between a first reflected signal and a second reflected signal and speed of sound within the heart wall.

In another embodiment of this aspect of the invention, the measuring step includes the step of measuring a dimension of the heart. In alternative the measuring step includes measuring impedance of a region of the heart.

In another aspect of the invention, a system for controlling end diastolic volume (EDV) of a natural heart is disclosed. The system includes a stress sensor constructed and arranged to measure a parameter related to the end diastolic volume of the heart. The stress sensor includes a transmitter constructed and arranged to emit sound waves into the heart, and a receiver constructed and arranged to detect sound waves reflected from tissue interfaces in the heart. The system also includes a pacemaker, responsive to the stress sensor, constructed and arranged to invoke systole when the parameter reaches a selected level, the parameter reaching the selected level prior to termination of diastole.

Advantageously, the present invention decreases or prevents dilation and, hence, thinning of the heart wall. This, in turn, provides the additional benefit of increasing the efficiency and work capacity of the heart.

Another advantage is that the present invention monitors the heart throughout the cardiac cycle and applies a pacing pulse to the heart to induce systole at a predetermined time so as to limit the ventricular volume at the end of diastole.

Another advantage of the present invention is that it controls congestive heart failure by maintaining the heart in its normal physiological state, going beyond those treatments that address only the symptoms of congestive heart failure.

A still further advantage of the present invention is that it electrically utilizes the heart muscle to effect systole, making the approach simpler and less invasive than conventional approaches.

Further features and advantages of the present invention, as well as the structure and operation of various embodiments of the present invention, are described in detail below with reference to the accompanying drawings.

BRIEF DESCRIPTION OF THE DRAWINGS

The present invention is described with reference to the accompanying drawings.

In the drawings, like reference numerals indicate identical or functionally similar elements.

DETAILED DESCRIPTION

Figure 1:
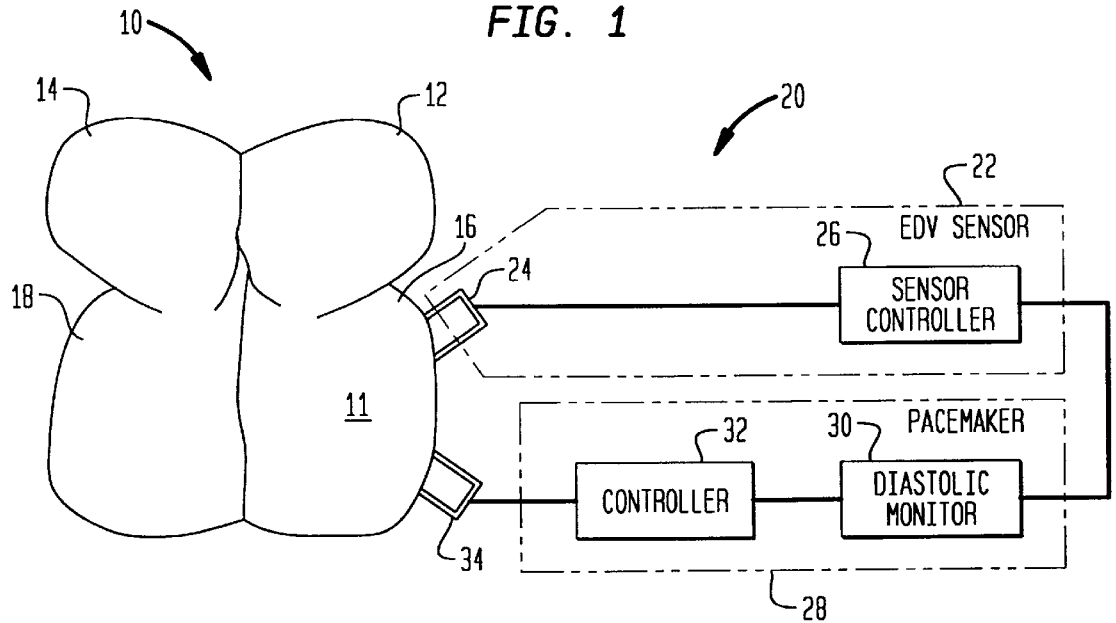
FIG. 1 is a block diagram of one embodiment of the system of the present invention for controlling ventricular dilation.

Referring to FIG. 1, a system 20 for controlling ventricular dilatation includes an EDV sensor 22 connected to a heart stimulator such as a pacemaker 28. The EDV sensor 22 includes a probe 24 located in contact with tissue of the heart 10 and connected to a sensor controller 26. EDV sensor 22 senses one or more physical parameters of the heart related to, for example, a dimension of the left or right ventricle during diastole. Then EDV sensor 22 provides signals to pacemaker 28, which induces systole before the natural end of diastole of the heart 10.

Pacemaker 28 provides pacing signals to the heart 10 via a set of pacing leads or electrodes 34 connected in a known manner to the wall of the left ventricle 16. Pacemaker 28 primarily includes a diastolic monitor 30 and a pacemaker controller 32. Diastolic monitor 30 receives signals from the EDV sensor 22 and provides data to pacemaker controller 32. Pacemaker controller 32 controls the timing of the pacing signals delivered to the left ventricle 16 by pacing leads 34. The diastolic monitor 30 and pacemaker controller 32 may be implemented as hardware, software, or any combination thereof in order to control the operation of pacemaker 28.

The operation of pacemakers such as pacemaker 28 is well known to a person of ordinary skill in the art. One such pacemaker which may be used in accordance with the present invention is described in U.S. Pat. No. 5,417,715, which is hereby incorporated by reference in its entirety as if fully set forth herein. Pacemaker 28 may employ an open loop design, where a sensor (for example, an EDV sensor, an impedance sensor or an activity sensor) detects a physiological change, which is converted to a signal intended to induce systole using a selected algorithm. The resultant change in the initiation of systole does not have a negative feedback effect on the monitored physiological property. Alternatively, pacemaker 28 may employ a closed loop design. In the closed loop design, the sensor detects a physiological change, which triggers a signal intended to induce systole using another selected algorithm, but the rate change alters the monitored physiological property in a desired direction. Pacemaker 28 may be any commercially available unit now or later developed. For example, the pacemaker 28 may be a Biorate® (manufactured by Biotec, S.P.A., Bologna, Italy), Meta® (manufactured by Telectronics Pacing Systems, Englewood, Colo.), Precept®, R.S4®, Excel® (all manufactured by Cardiac Pacemakers, Inc., St. Paul, Minn.), or Tx®, Quintech®, Rhythmyx® (all manufactured by Vitatron Medical B.V., Dieren, The Netherlands) pacemaker.

The EDV sensor 22 may be a stress sensor, a strain sensor, a dimension sensor, an impedance sensor, an optical sensor, a microwave sensor, or another sensor constructed to measure a parameter related to the end diastolic volume of the heart, or another selected physiological or pathophysiological condition or conditions of the heart.

Figure 2A:
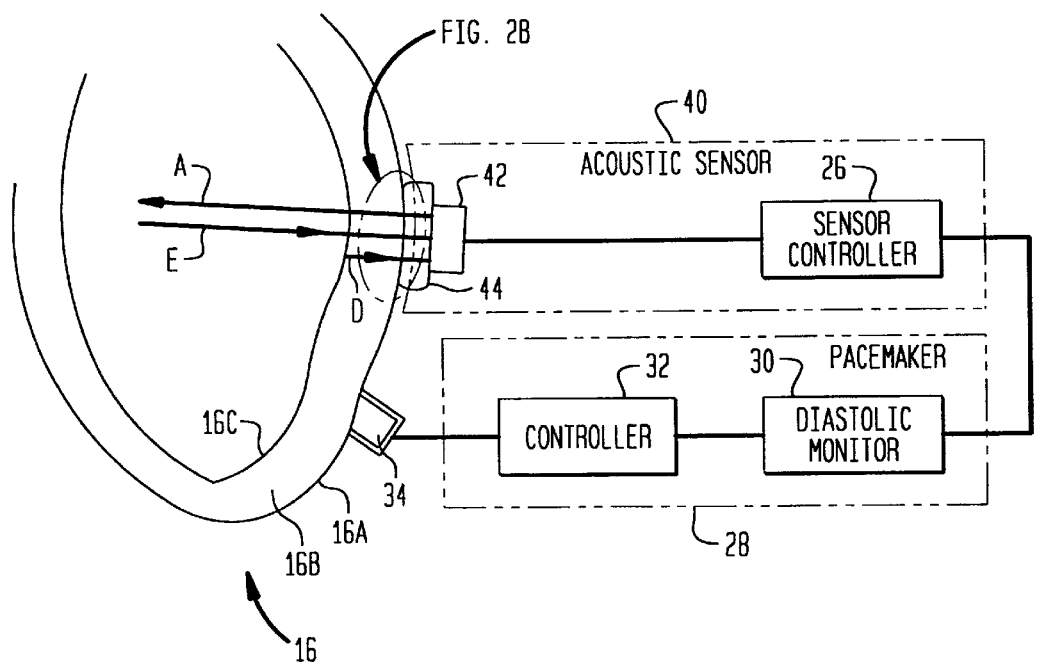
FIG. 2A is a schematic diagram of an acoustic sensor employed in one embodiment of the system shown in FIG. 1.
Figure 2B:
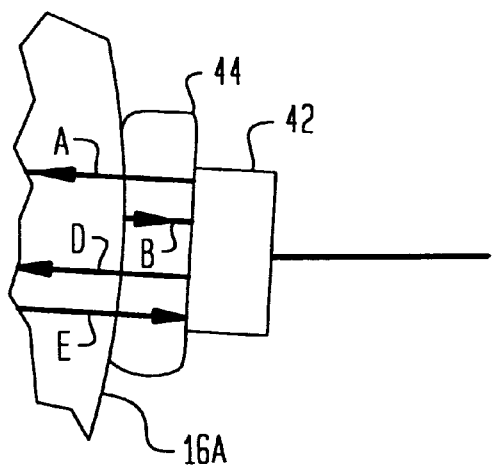
FIG. 2B is an exploded view of the signals transmitted from and received by the acoustic sensor shown in FIG. 2A.

Referring to FIGS. 2A and 2B, in one embodiment, the EDV sensor 22 is an acoustic sensor 40. The acoustic sensor 40 preferably includes one or more piezoelectric crystals 42, which are attached to a surface of the epicardium by a coupling medium 44 or is implanted within the myocardium. Coupling medium 44 is constructed and arranged to transmit acoustic waves to and receive reflected acoustic waves from the heart. The piezoelectric crystals 42 generate acoustic waves in response to stimulation signals from sensor controller 26, and detects acoustic waves reflected from different tissue interfaces in the heart. Based on the emitted and detected acoustic waves, acoustic sensor 40 calculates a selected physiological or pathophysiological condition of the heart.

Specifically, acoustic sensor 40 is employed as a stress sensor for monitoring the stress of the ventricular wall. One or more crystals 42 coupled to coupling medium 44 are attached to the epicardium 16a of the left ventricle 16. (In dilated cardiomyopathy, the left ventricular dilation is of most concern because the contractions of the left ventricle force blood through the circulatory system.) Piezoelectric crystal 42 generates sound waves transmitted into the left ventricle 16 filled with blood 11. Sound waves reflected from the different tissue interfaces in the heart propagate back to the piezoelectric crystal 42, where the time differences between emitted and detected pulses are proportional to ventricular dimensions. The induced pulse interval is processed by controller 26, which is in communication with pacemaker 28. Acoustic sensor 40 monitors the volume of the left ventricle by calculating the stress of the ventricular wall, which is related to the ventricular radius and wall thickness. The ventricular wall stress σ is determined using the following equation:

$$\sigma = \frac{Pr}{\tau} \quad (1)$$

where P is the ventricular pressure, r is the ventricular radius and τ is the ventricular wall thickness.

To determine the ventricular pressure, the rigidity of the epicardial surface during diastole is measured. The rigidity of the epicardium during diastole provides an indirect measure of the ventricular pressure. The rigidity can be expressed as the amplitude (a) of the vibration of the epicardium, which is a function of the phase angle φ. The amplitude (a) is given by:

$$a = \frac{F_0}{\sqrt{m^2(\omega_0^2 - \omega^2)^2 + \beta^2\omega^2}} \quad (2)$$

where $F_0$ is the mean transmitted force, $\omega_0$ is the driver frequency, and ω is the oscillating frequency of the epicardium. The pressure is proportional to the amplitude (a) for a given wall thickness (τ) and radius (r). Furthermore, the phase relationship of the driving force exerted by piezoelectric crystal 42 and the vibrations at the surface of a epicardium can be expressed as follows:

$$\tan\phi = \frac{\beta\omega}{m(\omega_0^2 - \omega^2)} \quad (3)$$

and, using the trigonometric identity $$\sin^2\phi = \frac{\tan^2\phi}{1+\tan^2\phi}, \quad (4)$$

the amplitude (a) is expressed as follows:

$$a = \frac{F_0}{\beta\omega}\sin\phi \quad (5)$$

This displacement measures the rigidity of the epicardium related directly to its natural resonance frequency that is sensed by piezoelectric crystal 42 as compression waves.

Figure 3:
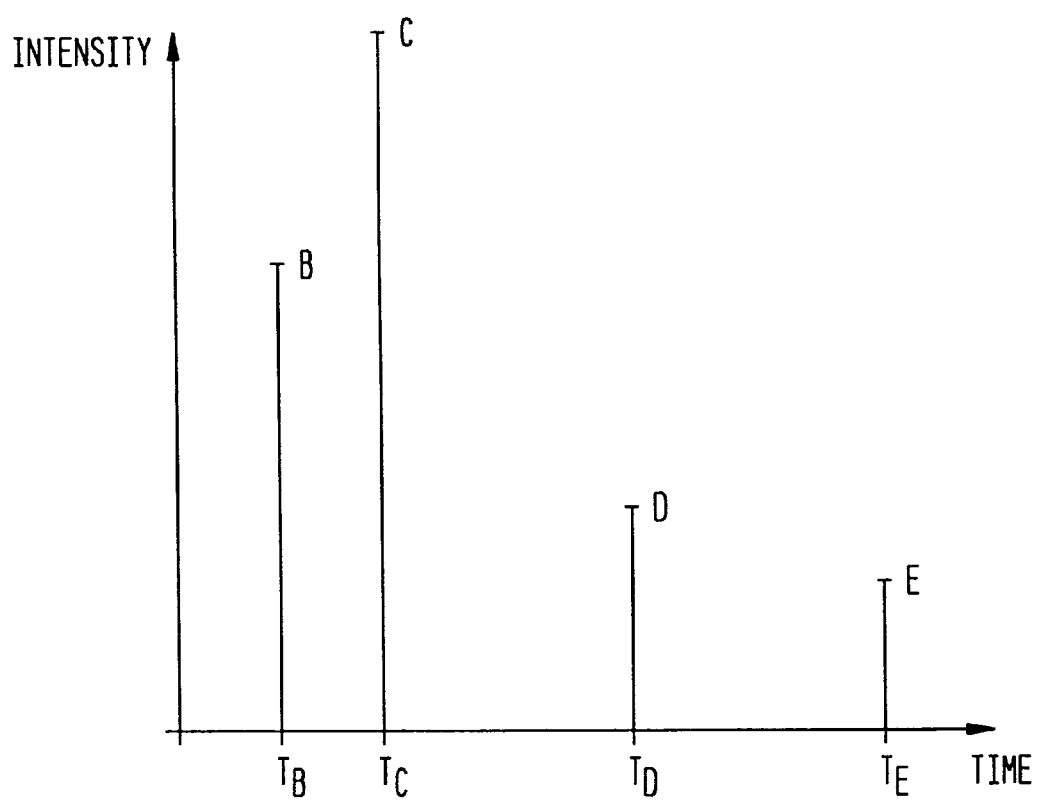
FIG. 3 shows graphically the intensity and timing of acoustic waves detected by the acoustic sensor of FIG. 2 after propagation in the heart.

The ventricular wall thickness ($\tau$) and the ventricular radius (r) are determined from acoustic waves reflected from the tissue interfaces inside the left ventricle. As shown in FIG. 2, piezoelectric crystal 42 emits acoustic wave (A) through the heart wall into the left ventricle 16. The first reflected wave (B) comes from a partial reflection of the introduced acoustic wave (A) at the coupling medium-epicardium interface 46. The second reflected wave (D) arises from a partial reflection at the first endocardium-blood interface 48, and the third signal (E) from a partial reflection at the second blood-endocardium interface 50. FIG. 3 illustrates the intensity vs. time dependence of the signals illustrated in FIG. 2B as they may be detected by piezoelectric crystal 42. The signal (C) shown in FIG. 3 appears from the resonance frequency and is distinct from reflected signals B, D and E.

The ventricular wall thickness $\tau$ is calculated as the product of the time elapsed between signal B and signal D, ($T_D$-$T_B$), and the speed of sound in the myocardium ($C_M$):

$$\tau = (T_D - T_B)C_M \quad (6)$$

The time elapsed between detected signal E and detected signal D is twice the time it takes the introduced signal (A) to travel across the ventricular volume. This time divided by 4 and multiplied by the speed of sound in blood ($C_B$) gives the ventricular radius r:

$$r = C_B\frac{(T_E - T_D)}{4} \quad (7)$$

As the heart dilates, the shape of the ventricles progresses from their normal, conical shape to a spherical shape. Thus, the ventricular radius (r) provides a good measure of the ventricular volume. Assuming a spherical heart-shape, the heart wall thickness is proportional to $1/r^2$ and the stress developed in the heart wall is proportional to $r^3$, assuming a constant mean ventricular pressure.

Sensor controller 26 calculates the ventricular wall stress based on the ventricular pressure (P), the ventricular radius (r), and the ventricular wall thickness ($\tau$) by employing Eq. 2. During the progressive dilatation of the heart, the size of the heart depends on the overall stress although local measurement of the wall stress varies since the heart wall is in a constant state of repair and modification. Heart wall stress is an important measure of the heart function. The stress must not exceed the peak active important measure of the heart function. The stress must not exceed the peak active tension developed by the sarcomeres, the fibers that make up the muscle of the heart wall. Several studies have shown that active tension in the heart wall does not increase when the sarcomeres are stretched beyond their normal length of approximately 2.1 to 2.3 micrometers. This is described in, for example, J. M. Guccione, A. D. McCulloch. *Mechanics of Active Contraction In Cardiac Muscle: Part I—Constructive Relations for Fiber Stress that Describe Deactivation*, J. BIOMED. ENG. 115 (1993), 72–81, or ter Keurs, H. E. D. J., Rijnsburger, W. H., Van Heuningen, R. and Nageismit, M. J. *Tension Development and Sarcomere Length In Rat Cardiac Trabeculae: Evidence of Length-Dependent Activation*, CIRC. RES. 46 (1980), 703–713, all of which are herein incorporated by reference in their entirety. Accordingly, once the heart begins to dilate, the relationship between the active tension and the sarcomere length in the heart wall is assumed to remain constant. A reduction in the heart radius before the occurrence of peak distension produces an increased stroke volume. After the heart wall stress due to dilation exceeds the peak active tension produced by the sarcomeres, there is a progressive diminution of the stroke volume. In other words, contractile force increases up to a peak active tension after which the available contractile force is reduced.

System 20 operates interactively to diagnose a heart condition and to adjust the heart rate accordingly. The sensor controller 26 provides the calculated stress value to diastolic monitor 30, which predicts the end of diastole. Pacemaker controller 32 receives one or more signals from the diastolic monitor 30 and determines when the pacing signal should be applied via pacing leads 34. The entire operation is controlled by a "smart" control algorithm, which can be partially or completely replaced by telemetry even after system 20 is implanted in a patient.

Figure 4:
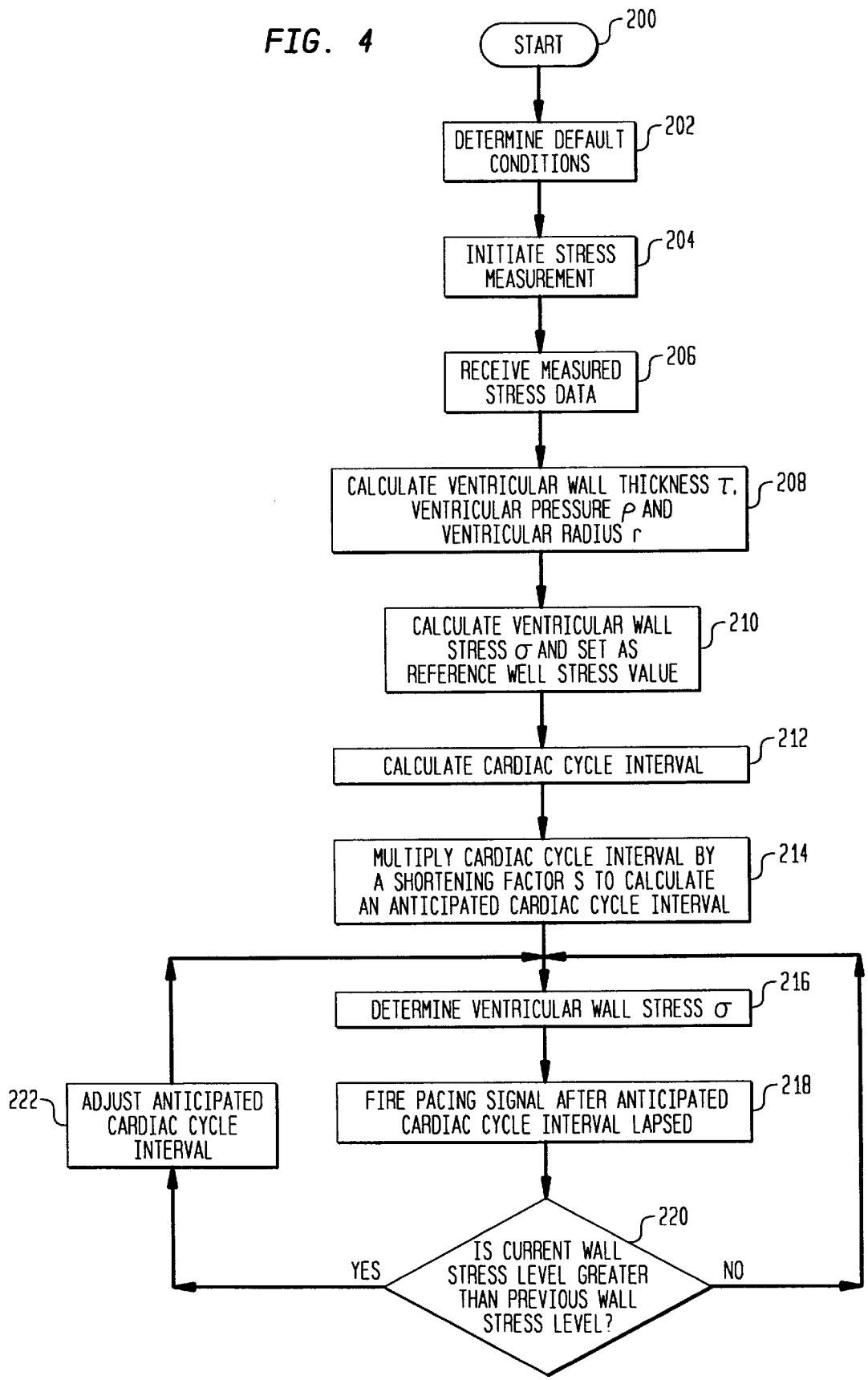
FIG. 4 is a conceptual flow diagram of an algorithm used by the system of FIG. 1.

Referring to FIG. 4, initially, the algorithm directs pacemaker controller 32 to determine default conditions (step 202). In step 204, diastolic monitor 30 instructs sensor controller 26 to initiate acoustic wave A and detect reflected acoustic waves B, D and E shown in FIG. 3. In step 206, sensor controller 26 receives from piezoelectric crystal 42 signals corresponding to the detected acoustic waves. Based on these signals, in step 208, sensor controller 26 calculates the ventricular wall thickness, $\tau$, the diastolic ventricular pressure, p, and the ventricular radius, r. Then sensor controller 26 calculates the ventricular wall stress $\sigma$ (step 208). Diastolic monitor 30 receives the stress value and sets this value as a reference value. In step 212, pacemaker controller 32 directs diastolic monitor 30 to determine a cardiac cycle interval. Pacemaker controller 32 receives the calculated cardiac cycle interval and multiplies it by a predetermined shortening factor S to set an anticipated cardiac cycle interval length (step 214). Pacemaker controller 32 directs a pulse generator to fire the pacing signal after the anticipated cardiac cycle interval length has lapsed (step 218). Diastolic monitor 30 requests and receives the ventricular stress data immediately prior to the firing of the pacing signal. Then diastolic monitor 30 compares the new stress data to the ventricular stress calculated prior to the previous pacing signal (step 220). If the ventricular stress is greater than it was prior to the immediately preceding pacing signal, pacemaker controller 32 shortens the pacing time to maintain the ventricular stress at a constant level (step 222). Alternatively, if the ventricular stress measurement yields a lower value than the previous measurement, pacemaker controller 32 lengthens the firing time to maintain the ventricular stress at that same constant level. System 20 performs periodic stress measurements and controls the cardiac cycle between the individual beats or over a number of beats.

In another embodiment, system 20 measures the volume of the left ventricle by measuring ventricular impedance.

The ventricular volume can be determined using the following equation:

$$V = \rho \frac{L^2}{R} \quad (8)$$

where V is the blood volume between a pair of sensing electrodes coupled to the heart, ρ is the resistivity of the blood, L is the distance between the sensing electrodes, and R is the magnitude of impedance between the sensing electrodes. Since the heart wall is in a constant state of repair and modification, wall stress is an improper indicator, by itself, of ventricular volume. Accordingly, in a preferred embodiment the volume as determined by the impedance is preferably supplemented by additional sensor data that provide additional measurements such as ventricular wall thickness, ventricular pressure and ventricular radius. For example, in one embodiment, the acoustic sensor data is utilized to accurately determine the stroke volume.

An alternative approach to assessing stress levels in the myocardium involves monitoring the QT interval by pacemaker 28 alone (or by EDV sensor 22 arranged for measuring electric potentials in the heart). The QT interval is the time which elapses between contraction of the heart muscle (Q wave) and repolarization of heart muscle cells (T wave). The paced QT is measured from the pacemaker spike, which occurs when a pacing signal is delivered, to the maximum negative deflection of the first derivative of the endocardial T wave. The QT interval is sensitive to heart rate and circulating catecholamines and may be directly derived from an intercardiac electrogram measured by pacing electrodes 34. When electrically pacing the heart, a large polarization effect is expected to occur after a pacing pulse. Thus system 20 includes waveform and post pulse compensation devices that eliminate the polarization effect and allow accurate determination of the QT interval.

In general, pacemaker 28 not only responds to data from EDV sensor 22, which monitors changes in the heart volume in accordance with an implemented embodiment of the present invention, but can also respond to other changes that affect the heart rate such as exercise or sleep. These changes are detected by an additional appropriate sensor (e.g., an exercise sensor, a temperature sensor) or are detected by employing pacing electrodes 34 connected to pacemaker 28. In such case, diastolic monitor 30 determines the cardiac cycle interval based on the QT interval. The QT interval shortens during physical exercise and mental stress, and thus the ventricular paced QT interval during exercise is shorter than when pacing the ventricle at a similar rate at rest. Pacemaker controller 32 may also monitor abnormal heart function. For example, in the absence of an EKG signal, the heart stimulator becomes a pacemaker that uses its original cardiac interval default value and a shortening factor S of 1. If the QT interval progressively shortens, a tachycardia-terminating sequence is triggered to restore the heart rate.

Figure 5:
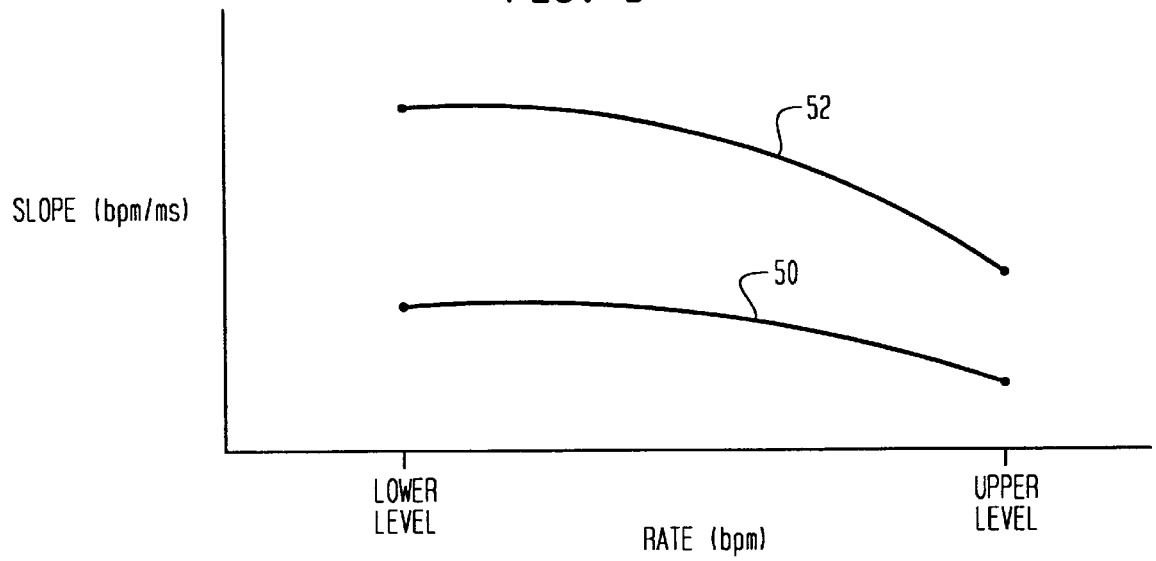
FIG. 5 shows a dependence of the QT interval slope on the heart rate employed in the system of FIG. 1.

To take into account a nonlinear QT/heart rate relationship, the QT interval is preferably measured at least two different rates at rest, and a slope is derived. An arbitrary 90% of the slope is programmed to be used as the lower rate limit. Since the QT interval changes are likely to be less at higher pacing rates, a slope declining factor can be programmed so that a lower slope is used when the pacing rate increases. This allows a more rapid change in pacing rate at the start of an activity, such as exercise, and avoids excessive rate acceleration as the upper rate is approached. The relationship between the QT interval slope and the heart rate is shown in FIG. 5. The initial slope/rate relationship detected by diastolic monitor 30 (shown in FIG. 1), is shown by line 50. Diastolic detection monitor 30 automatically adjusts the slope at the lower rate limit to obtain an optimized slope and automatically calculates the slope at the lower rate limit periodically, preferably daily. The slope is then automatically adjusted according to the measured value. The amount of change per day is limited to one step in the direction of outcome of the measurement to avoid excessive variability in the slope. This resulting slope is shown as line 52 in FIG. 5.

Optionally, pacemaker controller 32 provides for a rapid change in the pacing rate at the start of exercise, to avoid excessive rate acceleration as the upper rate is approached. The pacemaker controller 32 periodically (e.g., daily) adjusts the slope at the lower rate limit. The slope change is usually limited to one step in the direction of outcome of the measurement so that excessive daily slope variations do not occur. Similarly, if the QT interval continues to shorten when the upper rate is reached, the slope declining factor is increased by one step. This ensures a greater reduction in slope as the upper rate is approached. The upper rate will therefore be attained more slowly when exercise is again performed.

Figure 6:
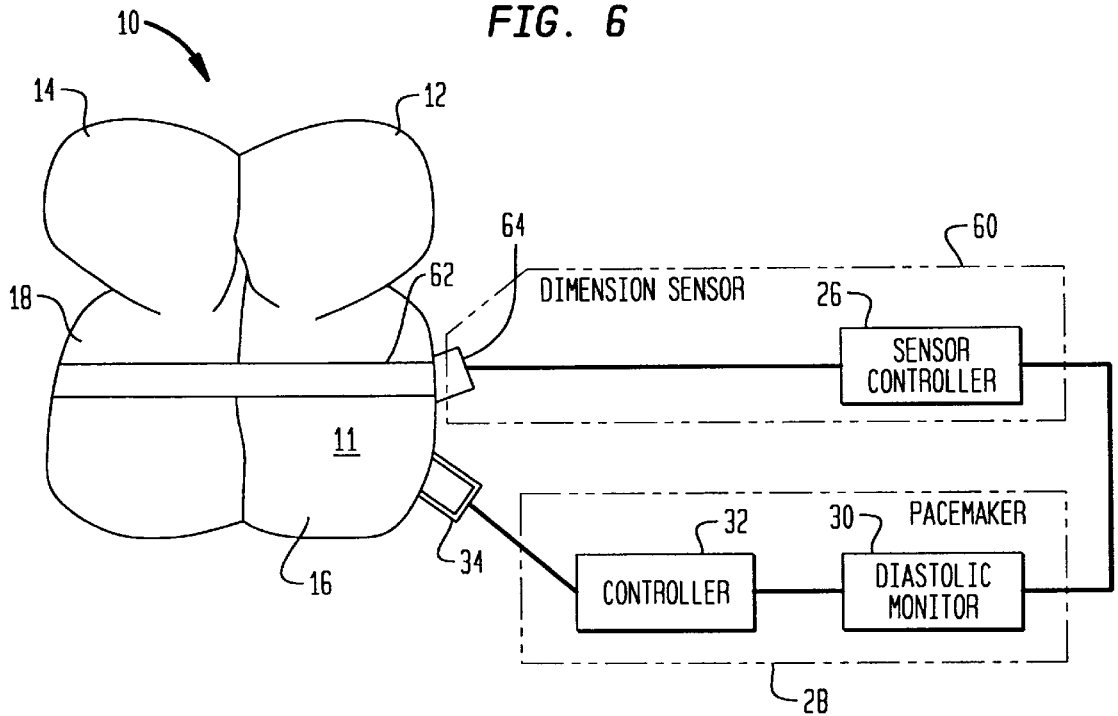
FIG. 6 is a schematic diagram of a dimension sensor employed in the system of FIG. 1.

Referring to FIG. 6, in another preferred embodiment EDV sensor 22 is a dimension sensor 60. Dimension sensor 60 includes a probe in the form of a wrap 62, which may be rigid or stretchable. Wrap 62, which at least partially encircles the heart, includes a strain-responsive measuring device 64. As the heart expands and contracts through the cardiac cycle, dimension sensor 60 measures the circumference of the heart. When the heart reaches a predetermined circumferential limit, a pacing pulse is applied to the heart in order to induce systole. In addition to measuring the circumference of the heart, wrap 62 may also provide a mechanical stop to retard or limit heart dilation. Preferably, wrap 62 is located around at least one ventricle to monitor the ventricular volume.

Figure 7:
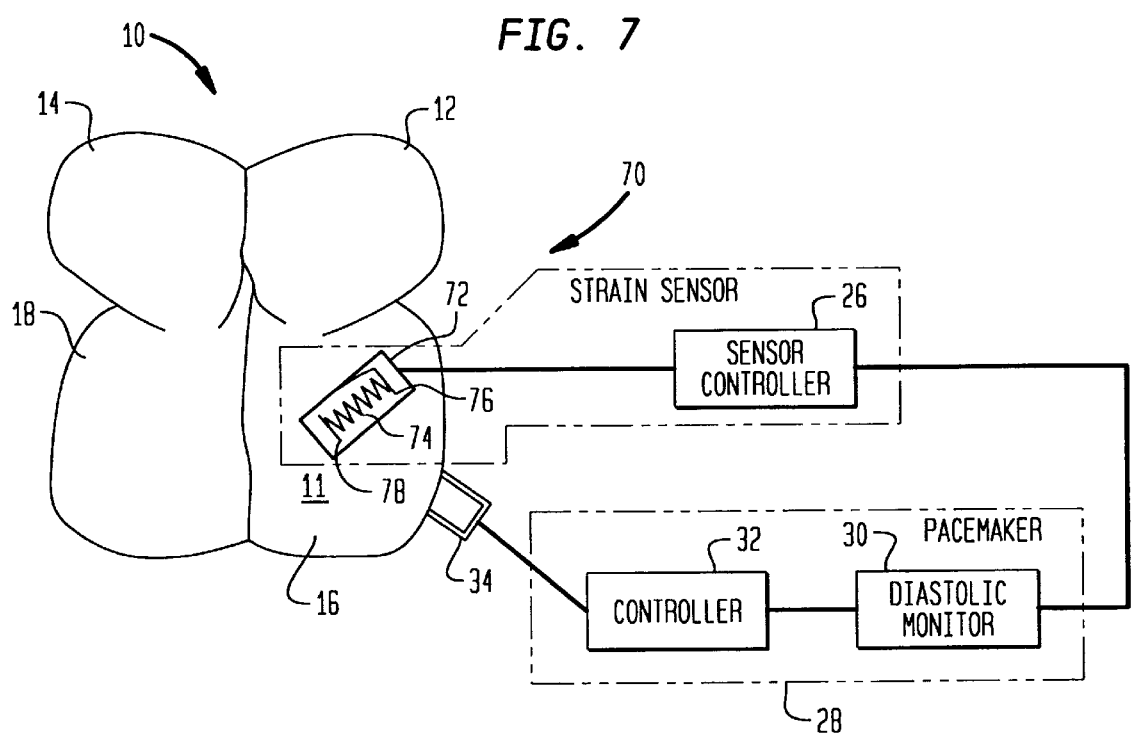
FIG. 7 is a schematic diagram of a strain sensor employed in the system of FIG. 1.

Referring to FIG. 7, in another preferred embodiment, EDV sensor 22 is a strain sensor 70. Strain sensor 70 includes a strain gage 72 and sensor controller 26. Strain gage 72 includes a strain responsive element 74 located between two fixed points 76 and 78. Strain gage 72 is attached to the heart wall 16. As the heart expands and contracts through the cardiac cycle, strain sensor 70 measures displacement of strain responsive element 74. Based on this displacement, strain sensor 70 determines the ventricular dilatation stroke volume of the ventricle, using an estimated or empirically determined stress/strain relationship, for example, given in Equation 5. Pacemaker 28 applies pacing pulses to the heart to induce early systole before end diastole to limit end diastolic volume. In short, after detecting the end diastole, the system maximizes the stroke volume by limiting the end diastolic volume.

Having now described several embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims.

What is claimed is:

1. A system for controlling end diastolic volume (EDV) of a natural heart to treat dilated cardiomyopathy comprising:
   an EDV sensor constructed and arranged to measure a parameter related to the end diastolic volume of the heart; and a heart stimulator to treat dilated cardiomyopathy, responsive to said EDV sensor, constructed and arranged to invoke systole when said parameter reaches a selected level, said parameter reaching said selected level prior to termination of diastole, and thereby inducing early systolic ejection before a maximum diastolic volume is reached.

2. The system of claim 1, wherein said heart stimulator is a pacemaker.

3. The system of claim 1, wherein said EDV sensor comprises a strain sensor.

4. The system of claim 3, wherein said strain sensor includes an expandable element implanted on a wall of the heart.

5. The system of claim 4, wherein said expandable element at least partially encircles the heart.

6. The system of claim 1, wherein said EDV sensor includes a stress sensor.

7. The system of claim 6, wherein said stress sensor comprises:
   a transmitter constructed and arranged to emit sound waves into the heart; and
   a receiver constructed and arranged to detect sound waves reflected from the heart.

8. The system of claim 7, wherein said transmitter and said receiver comprise at least one piezoelectric crystal.

9. The system of claim 8, wherein said stress sensor further comprises:
   a coupling medium attached to said piezoelectric crystal, said coupling medium being implantably attachable to a wall of the heart.

10. The system of claim 7, wherein said receiver is constructed and arranged to detect multiple sound waves reflected from tissue interfaces in the heart.

11. The system of claim 7, wherein said stress sensor is further constructed to measure stress within a myocardium of the heart, said stress sensor employing the following equation:

$$\sigma = \frac{Pr}{\tau}$$

where σ is the stress, P is ventricular pressure, r is ventricular radius and τ is ventricular wall thickness.

12. The system of claim 11, wherein said stress sensor is further constructed to calculate said ventricular thickness (τ) as a product of a time between a first reflected signal and a second reflected signal and speed of sound within the heart wall.

13. The system of claim 11, wherein said stress sensor is further constructed to calculate said ventricular radius (r) by employing the following equation:

$$r = \frac{T_E - T_D}{4} C_B$$

where $T_E$ is detected time of a third reflected signal, $T_D$ is detected time of a second reflected signal, and $C_B$ is speed of sound in blood.

14. The system of claim 1, wherein said EDV sensor comprises a dimension sensor.

15. The system of claim 14, wherein said dimension sensor comprises:
   a band that at least partially encircles the heart to monitor a circumference of the heart.

16. The system of claim 14, wherein said dimension sensor includes a band that at least partially encircles the heart, said band including a selected fixed circumference.

17. The system of claim 16, wherein said band is expandable through a range of circumferences, said range including said selected circumference.

18. The system of claim 1, wherein said EDV sensor includes an impedance sensor.

19. A method for controlling end diastolic volume (EDV) of a natural heart to treat dilated cardiomyopathy, comprising the steps of:
   measuring a parameter related to the end diastolic volume of the heart by employing a EDV sensor; and
   invoking systole, by employing a heart stimulator to treat dilated cardiomyopathy, before termination of diastole when said parameter reaches a predetermined level, to induce early systolic ejection before a maximum diastolic volume is needed.

20. The method of claim 19, wherein said measuring step comprises measuring strain experienced by an expandable element implanted on a wall of the heart.

21. The method of claim 19, wherein said measuring step comprises the step of:
   measuring stress in a wall of the heart.

22. The method of claim 21, wherein said stress measuring step includes the steps of:
   emitting from a transmitter sound waves into the heart; and
   detecting by a receiver sound waves reflected from the heart.

23. The method of claim 22, wherein said emitting and detecting steps include the step of:
   introducing said sound waves into a coupling medium implantably attached to the heart wall.

24. The method of claim 22, wherein said detecting step comprises the step of:
   detecting multiple sound waves reflected from tissue interfaces in the heart.

25. The method of claim 24, wherein said stress measuring step includes the step of:
   calculating myocardium stress by employing the following equation:

$$\sigma = \frac{Pr}{\tau}$$

where σ is the stress, P is ventricular pressure, r is ventricular radius and τ is ventricular wall thickness.

26. The method of claim 25, wherein said stress measuring step further includes the step of:
   calculating said ventricular radius (r) by employing the following equation:

$$r = \frac{T_E - T_D}{4} C_B$$

where $T_E$ is detection time of a third reflected signal, $T_D$ is detected time of a second reflected signal, and $C_B$ is the speed of sound in blood.

27. The method of claim 25, wherein said measuring step further comprises the step of:

calculating said ventricular thickness ($\tau$) as a product of an elapsed time between a first reflected signal and a second reflected signal and speed of sound within the heart wall.

28. The method of claim 19, wherein said measuring step comprises the step of measuring a dimension of the heart.

29. The method of claim 19, wherein said measuring step comprises measuring impedance of a region of the heart.

30. A system for controlling end diastolic volume (EDV) of a natural heart comprising:

a stress sensor constructed and arranged to measure a parameter related to the end diastolic volume of the heart, said stress sensor including,
   a transmitter constructed and arranged to emit sound waves into the heart, and
   a receiver constructed and arranged to detect sound waves reflected from tissue interfaces in the heart; and a pacemaker, responsive to said stress sensor, constructed and arranged to invoke systole when said parameter reaches a selected level, said parameter reaching said selected level prior to termination of diastole.

* * * * *